United States Patent
Stoneberg et al.

(10) Patent No.: US 11,465,332 B2
(45) Date of Patent: Oct. 11, 2022

(54) IMPRINTING TAPE, METHOD OF MANUFACTURE THEREOF AND ARTICLES COMPRISING THE SAME

(71) Applicants: SHARKLET TECHNOLOGIES, INC, Aurora, CO (US); COOK MEDICAL TECHNOLOGIES LLC, Bloomington, IN (US)

(72) Inventors: Ryan E. Stoneberg, Wheeling, IL (US); Walter S. Thielman, Palatine, IL (US)

(73) Assignees: SHARKLET TECHNOLOGIES, INC., Aurora, CO (US); COOK MEDICAL TECHNOLOGIES LLC, Bloomington, IN (US)

(*) Notice: Subject to any disclaimer, the term of this patent is extended or adjusted under 35 U.S.C. 154(b) by 541 days.

(21) Appl. No.: 16/333,027

(22) PCT Filed: Sep. 20, 2017

(86) PCT No.: PCT/US2017/052438
§ 371 (c)(1),
(2) Date: Mar. 13, 2019

(87) PCT Pub. No.: WO2018/057586
PCT Pub. Date: Mar. 29, 2018

(65) Prior Publication Data
US 2019/0202109 A1    Jul. 4, 2019

Related U.S. Application Data

(60) Provisional application No. 62/396,950, filed on Sep. 20, 2016.

(51) Int. Cl.
*B32B 3/26* (2006.01)
*B29C 59/02* (2006.01)
(Continued)

(52) U.S. Cl.
CPC .......... *B29C 59/021* (2013.01); *B29C 59/022* (2013.01); *B32B 3/10* (2013.01);
(Continued)

(58) Field of Classification Search
CPC ............... B32B 3/26; B32B 3/266; F16L 9/18
See application file for complete search history.

(56) References Cited

U.S. PATENT DOCUMENTS

| 5,592,975 A | * | 1/1997 | Wissmann | ............... F16L 7/00 138/112 |
| 2005/0089671 A1 | * | 4/2005 | Kubota | .................. B32B 5/022 428/143 |

(Continued)

FOREIGN PATENT DOCUMENTS

| CN | 2475915 Y | 2/2002 |
| CN | 103042365 A | 4/2013 |

(Continued)

OTHER PUBLICATIONS

International Search Report for International Application No. PCT/US2017/052438 ; International Filing Date: Sep. 20, 2017; dated Dec. 26, 2017; 5 pages.

(Continued)

*Primary Examiner* — William P Watkins, III
(74) *Attorney, Agent, or Firm* — Cantor Colburn LLP (57) ABSTRACT

Disclosed herein is a multilayered tape comprising a first layer; where the first layer comprises a first surface and second surface; the first surface of the first layer having a surface texture; a second layer; the second layer having a first surface and a second surface; where the first surface of the second layer is closer to the second surface of the first layer than the second surface of the second layer; where the
(Continued)

second surface of the second layer contains at least one partition that is parallel to a longitudinal direction of the multilayered tape.

18 Claims, 3 Drawing Sheets

(51) Int. Cl.
  *B32B 7/12*   (2006.01)
  *B32B 15/09*  (2006.01)
  *B32B 18/00*  (2006.01)
  *B32B 27/28*  (2006.01)
  *B32B 27/08*  (2006.01)
  *B32B 27/36*  (2006.01)
  *B32B 3/10*   (2006.01)
  *B32B 15/08*  (2006.01)
  *B32B 9/04*   (2006.01)

(52) U.S. Cl.
  CPC ............... *B32B 3/26* (2013.01); *B32B 7/12* (2013.01); *B32B 9/04* (2013.01); *B32B 15/08* (2013.01); *B32B 15/09* (2013.01); *B32B 18/00* (2013.01); *B32B 27/08* (2013.01); *B32B 27/28* (2013.01); *B32B 27/281* (2013.01); *B32B 27/36* (2013.01); *B32B 27/365* (2013.01); *B29C 2059/023* (2013.01); *B29K 2869/00* (2013.01); *B29K 2879/08* (2013.01); *B29K 2905/00* (2013.01); *B29K 2909/02* (2013.01)

(56) References Cited

U.S. PATENT DOCUMENTS

| | | |
|---|---|---|
| 2007/0184242 A1 | 8/2007 | Rodewald et al. |
| 2009/0104402 A1 | 4/2009 | Esaki |
| 2010/0119755 A1 | 5/2010 | Chung |
| 2010/0224312 A1 | 9/2010 | Tsubaki et al. |
| 2011/0317269 A1 | 12/2011 | Paolilli et al. |
| 2012/0319325 A1 | 12/2012 | Chung et al. |
| 2014/0178646 A1 | 6/2014 | Wolk et al. |
| 2015/0342725 A1 | 12/2015 | Cuevas et al. |
| 2016/0023503 A1 | 1/2016 | Saito |
| 2016/0123846 A1 | 5/2016 | Magin et al. |
| 2017/0152338 A1 | 6/2017 | Brennan et al. |
| 2017/0216543 A1 | 8/2017 | Magin et al. |
| 2018/0078423 A1 | 3/2018 | Magin et al. |
| 2018/0171157 A1 | 6/2018 | Magin et al. |
| 2018/0214600 A1 | 8/2018 | Magin et al. |
| 2019/0161627 A1 | 5/2019 | Brennan et al. |
| 2019/0224903 A1 | 7/2019 | Thielman et al. |
| 2019/0291308 A1 | 9/2019 | Harvey et al. |

FOREIGN PATENT DOCUMENTS

| | | |
|---|---|---|
| CN | 205219922 U | 5/2016 |
| JP | 63126088 A | 5/1988 |
| JP | 10196884 A | 7/1998 |
| JP | 2002035196 A | 2/2002 |
| JP | 2015217548 A | 12/2015 |
| WO | 2004086147 A2 | 10/2004 |

OTHER PUBLICATIONS

U.S. Appl. No. 16/332,918, filed Mar. 13, 2019.
Written Opinion for International Application No. PCT/US2017/052438; International Filing Date: Sep. 20, 2017; dated Dec. 26, 2017; 10 pages.
Extended European Search Report for EP Application No. 17853788.2; Report dated Mar. 5, 2020 (6 pages).
U.S. Appl. No. 16/346,957, filed May 2, 2019.

\* cited by examiner

IMPRINTING TAPE, METHOD OF MANUFACTURE THEREOF AND ARTICLES COMPRISING THE SAME

CROSS REFERENCE TO RELATED APPLICATIONS

This application is a National Stage application of PCT/US2017/052438, filed Sep. 20, 2017, which claims the benefit of U.S. Provisional Application No. 62/396,950, filed Sep. 20, 2016, both of which are incorporated by reference in their entirety herein.

BACKGROUND

Disclosed herein is a tape that can be used for imprinting micro-texturing on surfaces of tubes and cylinders during manufacturing. More specifically, disclosed herein is a tape that can be used for imprinting micro-texturing on surfaces of catheters during manufacturing.

Surfaces that have patterns and other forms of texturing (hereinafter "texturing") can be advantageously used to minimize the adhesion of living organisms and other forms of non-living matter (e.g., ice, dust, dirt, and the like) to the surface. The texturing can have dimensions that are selected to specifically prevent the adhesion of specific living organisms or non-living matter on the surface, while at the same time encouraging the growth of other organisms or the adhesion of other types of non-living matter to the surface.

For example, in order to prevent the growth of certain types of living organisms the dimensions of the texturing may have to be in the nanometer or in the micrometer range, while for preventing the growth of certain other types of organisms, the dimensions of the texturing may have to be in the millimeter or centimeter range. In another example, in order to facilitate the growth of certain types of living organisms the dimensions of the texturing may have to be in the nanometer or in the micrometer range, while for facilitating the growth of certain other types of organisms, the dimensions of the texturing may have to be in the millimeter or centimeter range. Reproducing this texturing on surfaces that are large in size (e.g., of the area of several square centimeters) or on surfaces that have a complex shape (e.g., a non-planar surface that is circular or spherical) is difficult.

It is therefore desirable to have methods that can reproduce the texturing on catheters that have large surface areas relative to the area of the pattern. It is also desirable to reproduce the texturing on surfaces that have complex shapes or disposed upon surfaces located in regions that are difficult to access.

SUMMARY

Disclosed herein is a multilayered tape comprising a first layer; where the first layer comprises a first surface and second surface; the first surface of the first layer having a surface texture; a second layer; the second layer having a first surface and a second surface; where the first surface of the second layer is closer to the second surface of the first layer than the second surface of the second layer; where the second surface of the second layer contains at least one partition that is parallel to a longitudinal direction of the multilayered tape.

Disclosed herein too is a method comprising disposing a first layer on a second layer to form a multilayered tape; where the first layer comprises a first surface and second surface; the first surface of the first layer having a surface texture; and where the second layer comprises a first surface and a second surface; where the first surface of the second layer is closer to the second surface of the first layer than the second surface of the second layer; where the second surface of the second layer contains at least one partition that is parallel to a longitudinal direction of the multilayered tape; and bonding the first layer to the second layer.

Disclosed herein too is a method comprising contacting a device with a multilayered tape, where the multilayered tape comprises a first layer; where the first layer comprises a first surface and second surface; the first surface of the first layer having a surface texture; a second layer; the second layer having a first surface and a second surface; where the first surface of the second layer is closer to the second surface of the first layer than the second surface of the second layer; where the second surface of the second layer contains at least one partition that is parallel to a longitudinal direction of the multilayered tape; transporting the device and a multilayered tape through a guide tube; the multilayered tube being disposed on an outer surface of the conduit between the conduit and the guide tube; where a longitudinal axis of the tape is substantially parallel to a longitudinal axis of the device; and transferring a texture from the template to the device as the device and the multilayer template are transported through the guide tube.

DETAILED DESCRIPTION

Disclosed herein is a multilayered tape for imparting a texture to a surface during manufacturing. In an embodiment, the multilayered tape may also be used to impart texture to a flat surface or to a curved surface during manufacturing. Flat surfaces can include film surfaces while curved surfaces can include surfaces of conduits, cylinders, spheres, and the like. The tape comprises at least two layers—a first layer that contains the texture to be imparted to the conduit and a second layer that is disposed on the first layer and that serves to impart stability to the first layer during high temperature manufacturing processes. An optional third layer that comprises an adhesive may be disposed between the first layer and the second layer.

In an embodiment, the first layer and the second layer both are stable at high temperatures greater than or equal to 100° C., preferably greater than or equal to 150° C. and more preferably greater than or equal to 200° C. and can therefore impart the texture to the conduit during a manufacturing process that involves elevated temperatures greater than 100° C. High temperature stability implies that the multilayered tape does not lose its dimensional stability or begin to degrade during the manufacturing process or after the process. The multilayered tape is therefore reusable.

Figure 1:
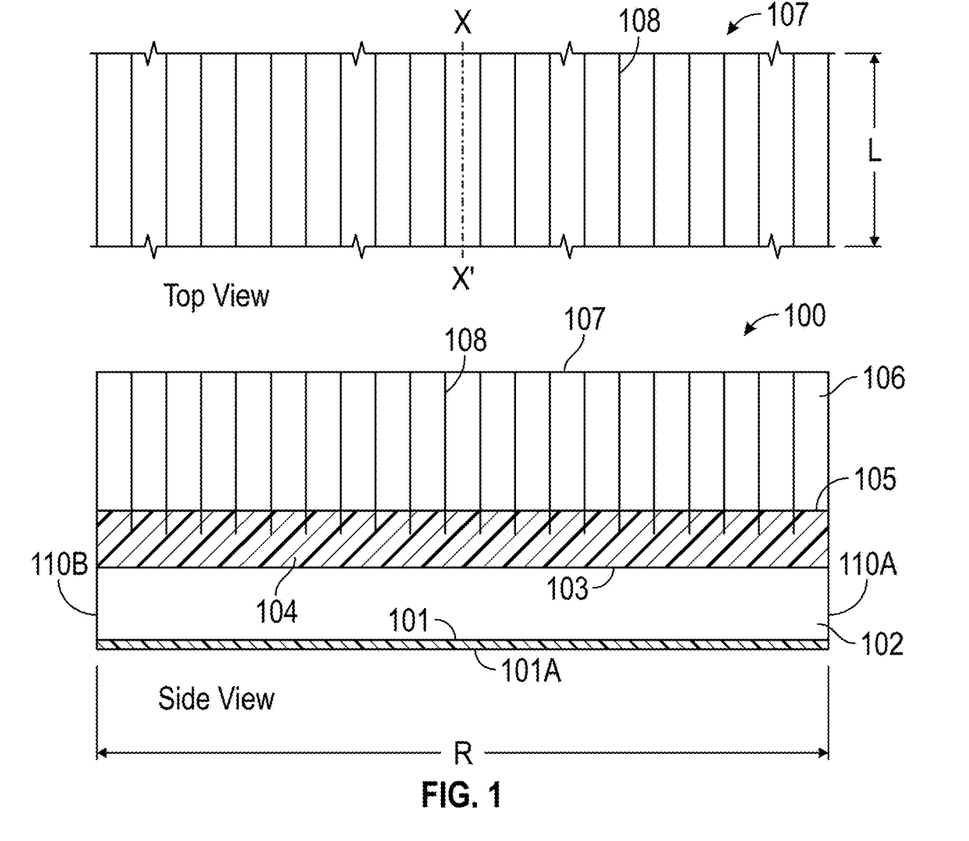
FIG. 1 is a schematic depiction of a top view and a side view of an exemplary multilayered tape that is used to impart textures to a surface.
Figure 2:
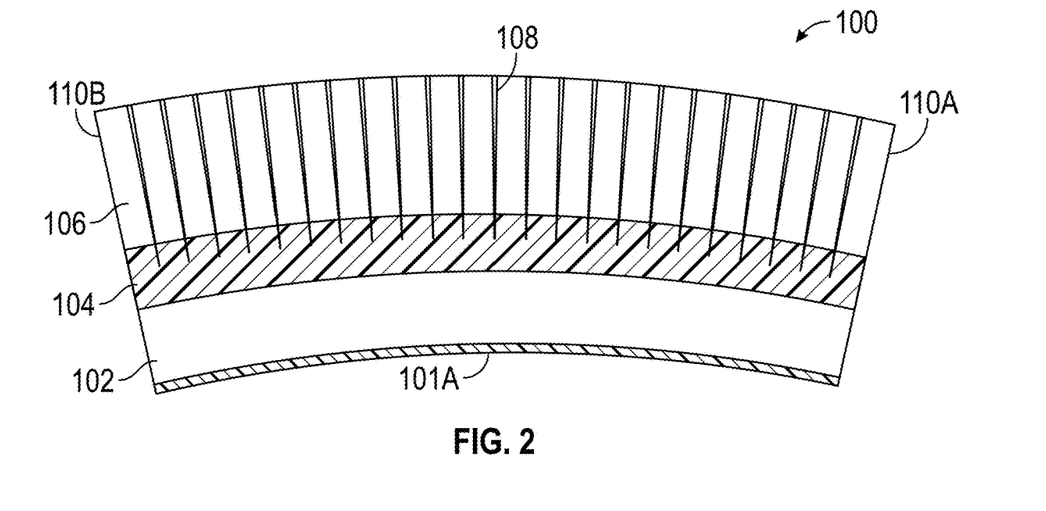
FIG. 2 is another schematic depiction of an exemplary multilayered tape that is used to impart texture to a surface when it is curved to texture a curved surface.
Figure 3A:
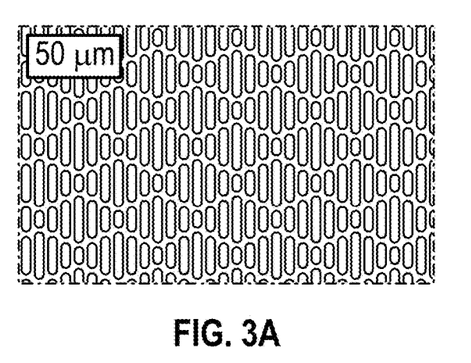
FIG. 3(A) depicts one possible texture that is imparted by the multilayered tape to a surface.
Figure 3B:
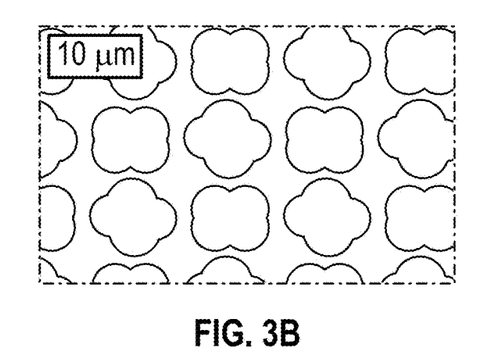
FIG. 3(B) depicts another possible texture that is imparted by the multilayered tape to a surface.
Figure 3C:
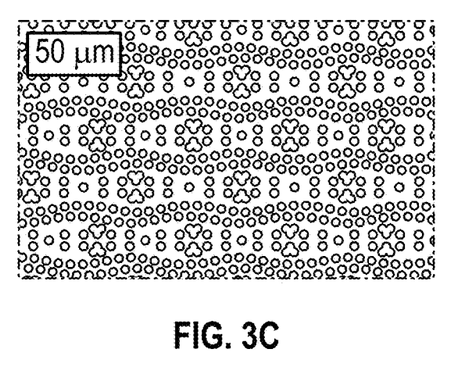
FIG. 3(C) depicts another possible texture that is imparted by the multilayered tape to a surface.
Figure 3D:
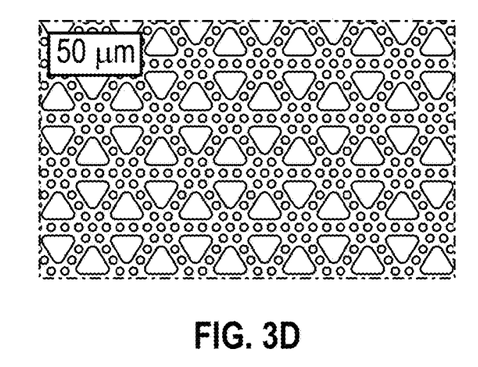
FIG. 3(D) depicts another possible texture that is imparted by the multilayered tape to a surface.

FIG. 1 and FIG. 2 are depictions of the multilayered tape 100 that is used to impart textures 101A to a surface of a device. In an exemplary embodiment, depicted in the FIG. 2, the multilayered tape 100 may be deformed to occupy a circular or semi-circular cross-sectional area that can impart a texture to the outer curved surface of a device (e.g., a tube, a conduit, a cylinder) during manufacturing.

With reference now to the FIG. 1, the multilayered tape 100 comprises a first layer 102 that contacts an optional third layer 104 which in turn contacts a second layer 106. The first layer 102 has a first surface 101 that contains the surface texture 101A that is imparted to a device that is to be textured. The surface texture 101A will be detailed later. As can be seen in the FIG. 1, the first layer 102 has a first surface 101 and a second surface 103. The second layer has a first surface 105 and a second surface 107. The first surface 101 of the first layer 102 has the surface texture 101A while the outer surface 107 of the second layer contains one or more partitions 108, which will be discussed later. From the FIG. 1, it may be seen that the first surface 105 of the second layer 106 is closer to the second surface 103 of the first layer 102 than the second surface 107 of the second layer 106. In an embodiment, the second surface 103 of the first layer 102 may be in direct contact with the first surface 105 of the second layer 106.

The first layer 102 has a lower softening temperature than the second layer 106 and the third layer 104. The optional third layer 104 is preferably an adhesive layer that bonds the first layer 102 to the second layer 106. The second layer 106 has at least one partition 108 in its outer surface such that when the multilayer tape 100 is wound round a cylinder or a conduit the outer circumferential surface of the multilayer tape 100 can expand significantly when compared with the inner circumferential surface of the tape 100.

In an embodiment, the second layer 106 may contain a plurality of partitions. The partitions 108 are also called slits and extend along the longitudinal direction XX' of the tape 100. The longitudinal direction is parallel to the length of the tape. The partitions 108 extend along the entire length of the multilayered tape 100. The outer surface 107 of the multilayer tape 100 expands relative to the inner surface 101 when disposed on a curved surface because the partitions 108 expand. This feature permits uniform and continuous contact of the surface texture 101A with the surface of the device that is to be textured.

As may be seen in the FIG. 1, the multilayer tape has a length "L" that can be greater than 50 centimeters, greater than 1 meter, greater than 2 meters, and preferably greater than 3 meters. The multilayer tape has a width "R" of a value that is effective to wind the tape around the outer perimeter of a cylinder or a conduit till the end 110A contacts the end 110B. In an embodiment, the width "R" may range from 5 millimeters to 50 centimeters. It may be greater than 50 centimeters if very large surfaces are to be textured. This may be more clearly seen in the FIGS. 4 and 5, which will be discussed later.

The layer 102 is manufactured from a composition that has a higher softening temperature than that of the surface material that it is imparting texture to. It however has a lower softening temperature than that of the material used in layers 104 and 106. In an embodiment, the softening temperature is the glass transition temperature. The layer 102 generally comprises an organic polymer. In an embodiment, the organic polymer used in the layer 102 has at least one glass transition temperature greater than 100° C., preferably greater than 110° C. and more preferably greater than 120° C. In an exemplary embodiment, the glass transition temperature is greater than 140° C.

Organic polymers may comprise thermosets, thermoplastics or a combination comprising at least one of a thermoset or a thermoplastic. The organic polymer may comprise a block copolymer, a diblock copolymer, a star block copolymer, a triblock copolymer, a dendrimer, an ionic copolymer, a polyelectrolyte, or the like.

Examples of thermoplastic polymers are polyacetals, polyolefins, polycarbonates, polyesters, polyamides, polyamideimides, polyarylates, polyarylsulfones, polyethersulfones, polyphenylene sulfides, polysulfones, polyimides, polyetherimides, polytetrafluoroethylenes, polyetherketones, polyether etherketones, polyether ketone ketones, polybenzoxazoles, polyphthalamides, polyvinyl ketones, polyvinyl halides, polyvinyl nitriles, polyvinyl esters, polysulfonates, polysulfides, polythioesters, polysulfonamides, polyureas, polyphosphazenes, polysilazanes, polytetrafluoroethylene, fluorinated ethylene propylene, perfluoroalkoxyethylene, polychlorotrifluoroethylene, polyvinylidene fluoride, or the like, or a combination thereof.

Examples of thermosetting polymers suitable for use in the layer 102 include epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, or the like, or a combination thereof.

Examples of blends of thermoplastic polymers include acrylonitrile-butadiene-styrene/nylon, polycarbonate/acrylonitrile-butadiene-styrene, acrylonitrile butadiene styrene/polyvinyl chloride, polyphenylene ether/polystyrene, polyphenylene ether/nylon, polysulfone/acrylonitrile-butadiene-styrene, polycarbonate/thermoplastic urethane, polycarbonate/polyethylene terephthalate, polycarbonate/polybutylene terephthalate, thermoplastic elastomer alloys, nylon/elastomers, polyester/elastomers, polyethylene terephthalate/polybutylene terephthalate, acetal/elastomer, styrene-maleic anhydride/acrylonitrile-butadiene-styrene, polyether etherketone/polyethersulfone, polyether etherketone/polyetherimide polyethylene/nylon, polyethylene/polyacetal, or the like.

An exemplary thermoplastic polymer comprises polycarbonate. The first layer has a thickness of 5 to 75 micrometers, preferably 10 to 60 micrometers and more preferably 15 to 45 micrometers.

The surface 101 of the first layer 102 is contains surface texture 101A. The surface texture 101A comprises a plurality of patterns. In one embodiment, the pattern generally has some features that are of the order of a few nanometers to several hundreds of millimeters in size. Each pattern is defined by a plurality of spaced apart features attached to or projected into the surface texture 101A. The plurality of features on the surface each has at least one neighboring feature that has a substantially different geometry or a substantially different size. The average spacing between adjacent features on the surface texture 101A is between about 1 nanometer to about 1 millimeter in at least a portion of the curved surface.

In one embodiment, when surface texture 101A is viewed in a first direction, the plurality of spaced apart features is represented by a periodic function. In another embodiment, the plurality of spaced apart features forms a pattern. Each pattern is separated from a neighboring pattern by a pathway that has a periodicity to it. The periodicity of this pathway may be sinusoidal. Non-limiting examples of the texture present on the surface texture 101A are shown in the FIGS. 3(A), 3(B), 3(C) and 3(D).

In one embodiment, the surface texture 101A can comprise a pattern that comprises a plurality of spaced features. The spaced features are arranged in a plurality of groupings. The groupings of features comprise repeat units that can be repeated laterally and longitudinally across the surface. The spaced features within a grouping are spaced apart at an average distance of about 1 nanometer to about 500 micrometers. Each spaced feature has a surface that is substantially parallel to a surface on a neighboring feature. Each feature is separated from a neighboring feature and the groupings of features are arranged with respect to one another so as to define a tortuous pathway.

In yet another embodiment, the surface texture 101A comprises a plurality of spaced features. The features are arranged in a plurality of groupings such that the groupings of features comprise repeat units. The spaced features within a grouping are spaced apart at an average distance of about 1 nanometer to about 500 micrometers. The groupings of features are arranged with respect to one another so as to define a tortuous pathway where a tangent to the tortuous pathway intersects with a spaced feature. The spaced feature is different in geometry (shape or size) from each nearest neighbor and is not in contact with the nearest neighbor.

In yet another embodiment, the surface texture 101A has a topography that comprises a pattern defined by a plurality of spaced apart features attached to or projected into a base surface of the layer 102. The plurality of features comprise at least one feature having a substantially different geometry, wherein neighboring patterns share a common feature, the plurality of spaced apart features having at least one dimension that is about 1 nanometer to about 1,000 micrometers. The neighboring spaced apart features can be spaced apart by a distance of about 5 nanometers to about 500 micrometers, specifically about 10 nanometers to about 100 micrometers, specifically about 1 micrometer to about 50 micrometers, and more specifically about 2 micrometers to about 25 micrometers.

In yet another embodiment, the surface texture 101A comprises a plurality of spaced features; the features being arranged in a plurality of groupings; the groupings of features comprising repeat units; the spaced features within a grouping being spaced apart at an average distance of about 1 nanometer to about 200 millimeters. The groupings of features are arranged with respect to one another so as to define a tortuous path. In one embodiment, a tangent to the tortuous path intersects with at least one of the features.

In one embodiment, when viewed in a second direction, the pathway between the features may be non-linear and non-sinusoidal. In other words, the pathway can be non-linear and aperiodic. In another embodiment, the pathway between the features may be linear but of a varying thickness. The plurality of spaced features may be projected outwards from a surface or projected into the surface. In one embodiment, the plurality of spaced features may have the same chemical composition as the surface. In another embodiment, the plurality of spaced features may have a different chemical composition from the surface.

The tortuous pathway may be represented by a periodic function. The periodic functions may be different for each tortuous pathway. In one embodiment, the patterns can be separated from one another by tortuous pathways that can be represented by two or more periodic functions. The periodic functions may comprise a sinusoidal wave. In an exemplary embodiment, the periodic function may comprise two or more sinusoidal waves.

In another embodiment, when a plurality of different tortuous pathways are represented by a plurality of periodic functions respectively, the respective periodic functions may be separated by a fixed phase difference. In yet another embodiment, when a plurality of different tortuous pathways are represented by a plurality of periodic functions respectively, the respective periodic functions may be separated by a variable phase difference.

In another embodiment, the topography of the surface texture 101A has an average roughness factor (R) of from 2 to 50.

In one embodiment, each feature of a pattern has at least one neighboring feature that has a different geometry (e.g., size or shape). A feature of a pattern is a single element. Each feature of a pattern has at least 2, 3, 4, 5, or 6 neighboring features that have a different geometry from the feature. In one embodiment, there are at least 2 or more different features that form the pattern. In another embodiment, there are at least 3 or more different features that form the pattern. In yet another embodiment, there are at least 4 or more different features that form the pattern. In yet another embodiment, there are at least 5 or more different features that form the pattern.

In another embodiment, at least two identical features of the pattern have at least one neighboring feature that has a different geometry (e.g., size or shape). A feature of a pattern is a single element. In one embodiment, two identical features of the pattern have at least 2, 3, 4, 5, or 6 neighboring features that have a different geometry from the identical features. In another embodiment, three identical features of the pattern have at least 2, 3, 4, 5, or 6 neighboring features that have a different geometry from the identical features.

In another embodiment, each pattern has at least one or more neighboring patterns that have a different size or shape. In other words, a first pattern can have a second neighboring pattern that while comprising the same features as the first pattern can have a different shape from the first pattern. In yet another embodiment, each pattern has at least two or more neighboring patterns that have a different size or shape. In yet another embodiment, each pattern has at least three or more neighboring patterns that have a different size or shape. In yet another embodiment, each pattern has at least four or more neighboring patterns that have a different size or shape.

The optional adhesive layer 104 contacts the first layer 102 at a surface 103 that is located opposite to the surface 101 that contains the surface texture 101A. The optional adhesive layer 104 generally comprises a thermoplastic polymer and/or a thermosetting polymer that can withstand manufacturing temperatures and can keep the first layer 102 bonded to the second layer 106.

Any of the thermoplastic or thermosetting polymers listed above may be used as the adhesive layer 104. The adhesive may be thermally curable or may be cured using electromagnetic radiation (e.g., xrays, ultraviolet light, electron beam radiation, and the like). A preferred adhesive is a silicone adhesive, an acrylate adhesive or an epoxy resin adhesive. In an exemplary embodiment, the third layer 104 is crosslinked.

Suitable silicone adhesives are represented by the structure of Formula (1) below.

$$R^B\text{—}[O\text{—}[Si(R^A)_2]_n\text{—}R^B \quad (1)$$

wherein n is an integer from 1 to 10,000, or from 2,000 to 8,000, or from 5,000 to 7,000; each $R^A$ is independently hydrogen, or an alkyl group having from 1 to 6 carbon atoms, or an alkyl group having from 1 to 3 carbon atoms; and each $R^B$ is independently hydrogen, an epoxy group, an ethylenically unsaturated group, a thiol group, an alkoxy group, or the like. In an embodiment, $R^A$ is independently —H, or —$C_xH_{2x+1}$, wherein each x is independently 1 to 6, or independently 1 to 3. In an embodiment, each $R^A$ is —$CH_3$. It is desirable for $R^A$ to not be an aromatic group.

The silicon adhesive can be a room temperature vulcanizate (RTV) silicone, including a two-component RTV curing system including a silicone rubber compound and curing agent. The silicon adhesive can be RTV615. The silicon adhesive can remain flexible at temperatures of –115 to 204° C. The silicone polymer can have a viscosity prior to curing between 3,000 and 7,000 centipoise (cps) at 23° C., preferably between 3,500 and 4,500 cps at 23° C.

Useful acrylate molecules are those represented by Formula (2):

(2)

where $R_1$ is a hydrogen, an alkyl group having 1 to 10 carbon atoms, a fluoroalkyl group having 1 to 10 carbon atoms and where $R_1'$ is hydrogen, a five membered ring or a six membered ring having at least one heteroatom, where the heteroatom is oxygen, nitrogen, sulfur, or phosphorus; or is a monomer represented by Formula (3):

(3)

where $R_1$ is a hydrogen, an alkyl group having 1 to 10 carbon atoms, or a fluoroalkyl group having 1 to 10 carbon atoms; where $R_1'$ is hydrogen, a five membered ring or a six membered ring having at least one heteroatom, where the heteroatom is oxygen, nitrogen, sulfur, or phosphorus; and where $R_2$ is a $C_{1-30}$ alkyl, $C_{3-30}$ cycloalkyl, $C_{6-30}$ aryl, $C_{7-30}$ alkaryl, $C_{7-30}$ aralkyl, $C_{1-30}$ heteroalkyl, $C_{3-30}$ heterocycloalkyl, $C_{6-30}$ heteroaryl, $C_{7-30}$ heteroalkaryl, $C_{7-30}$ heteroaralkyl, a $C_{2-10}$ fluoroalkyl group, an alkylene oxide, or a combination comprising at least one of the foregoing groups.

In another embodiment, the acrylate is a monomer represented by Formula (4):

(4)

where $R_1$ is a hydrogen, an alkyl group having 1 to 10 carbon atoms, or a fluoroalkyl group having 1 to 10 carbon atoms; where $R_1'$ is hydrogen, a five membered ring or a six membered ring having at least one heteroatom, where the heteroatom is oxygen, nitrogen, sulfur, or phosphorus; where at least one of $R_3$, $R_4$ and $R_5$ is a $C_{1-30}$ alkyl, $C_{3-30}$ cycloalkyl, $C_{6-30}$ aryl, $C_{7-30}$ alkaryl, $C_{7-30}$ aralkyl, $C_{1-30}$ heteroalkyl, $C_{3-30}$ heterocycloalkyl, $C_{6-30}$ heteroaryl, $C_{7-30}$ heteroalkaryl, $C_{7-30}$ heteroaralkyl, a $C_{2-10}$ fluoroalkyl group, an alkylene oxide, or a combination comprising at least one of the foregoing groups, where each of the groups is covalently bonded to one or more vinyl groups.

The epoxy adhesive may be an aromatic, aliphatic or cycloaliphatic epoxy resin. In an embodiment, a useful epoxy resin is the diglycidyl ether of bisphenol F, also known as Epon 862® and having the structure shown in Formula (5):

(5)

In another embodiment, the epoxy resin is a modified diglycidyl ether of bisphenol F also known as a modified EPON 862® and having the structure shown in Formula (6):

(6)

where n is the number of repeat units. The epoxy resin of the formula (6) is produced by polymerizing bisphenol F with the EPON 862.

In an embodiment, the epoxy resin may have the structure shown in the Formula (7) below:

(7)

where $R_1$ is a single bond, —O—, —S—, —C(O)—, or a $C_{1-18}$ organic group. The $C_{1-18}$ organic bridging group may be cyclic or acyclic, aromatic or non-aromatic, and can further comprise heteroatoms such as halogens, oxygen, nitrogen, sulfur, silicon, or phosphorus. The $C_{1-18}$ organic group can be disposed such that the $C_6$ arylene groups connected thereto are each connected to a common alkylidene carbon or to different carbons of the $C_{1-18}$ organic bridging group. In the Formula (6), $R_2$ is a $C_{1-30}$ alkyl group, a $C_{3-30}$ cycloalkyl, a $C_{6-30}$ aryl, a $C_{7-30}$ alkaryl, a $C_{7-30}$ aralkyl, a $C_{1-30}$ heteroalkyl, a $C_{3-30}$ heterocycloalkyl, a $C_{6-30}$ heteroaryl, a $C_{7-30}$ heteroalkaryl, a $C_{7-30}$ heteroaralkyl, a $C_{2-10}$ fluoroalkyl group, or a combination thereof.

In yet another exemplary embodiment, the epoxy resin is the reaction product of 2-(chloromethyl)oxirane and 4-[2-(4-hydroxyphenyl)propan-2-yl]phenol also known as bisphenol A-epichlorohydrin based epoxy (also known as bisphenol A diglycidyl ether) of the Formula (8) below:

(8)

The epoxy resin of Formula (8) is commercially available as EPON 828. Other exemplary variations of Formula (7) that may be used are shown in the Formulas (9) and (10). In an embodiment, one variation of the Formula (6) that may be used is shown in the Formula (9) below.

(9)

where $R_1$ is detailed above in Formula (7), $R_2$ and $R_3$ may be the same or different and are independently a $C_{1-30}$ alkyl group, a $C_{3-30}$ cycloalkyl, a $C_{6-30}$ aryl, a $C_{7-30}$ alkaryl, a $C_{7-30}$ aralkyl, a $C_{1-30}$ heteroalkyl, a $C_{3-30}$ heterocycloalkyl, a $C_{6-30}$ heteroaryl, a $C_{7-30}$ heteroalkaryl, a $C_{7-30}$ heteroaralkyl, a $C_{2-10}$ fluoroalkyl group, or a combination thereof.

In an exemplary embodiment, an epoxy having the structure of Formula (10) may be used in the composition.

(10)

Examples of suitable epoxies are diglycidyl ether of bisphenol A, diomethane diglycidyl ether, 2,2-bis(4-glycidyloxyphenyl)propane, 2,2'-((1-methylethylidene)bis(4,1-phenyleneoxymethylene))bisoxirane, 2,2-bis(4-(2,3-epoxypropyloxy)phenyl)propane, 2,2-bis(4-hydroxyphenyl)propane, diglycidyl ether, 2,2-bis(p-glycidyloxyphenyl)propane, 4,4'-bis(2,3-epoxypropoxy)diphenyldimethylmethane, 4,4'-dihydroxydiphenyldimethylmethane diglycidyl ether, 4,4'-isopropylidenebis(1-(2,3-epoxypropoxy)benzene), 4,4'-isopropylidenediphenol diglycidyl ether, bis(4-glycidyloxyphenyl)dimethylmethane, bis(4-hydroxyphenyl)dimethylmethane diglycidyl ether, diglycidyl ether of bisphenol F, 2-(butoxymethyl)oxirane, the reaction product of 2-(chloromethyl)oxirane and 4-[2-(4-hydroxyphenyl)propan-2-yl]phenol also known as bisphenol A-epichlorohydrin based epoxy, modified bisphenol A-epichlorohydrin based epoxy, diglycidyl 1,2-cyclohexanedicarboxylate, 1,4-cyclohexanedimethanol diglycidyl ether, a mixture of cis and trans 1,4-cyclohexanedimethanol diglycidyl ether, neopentyl glycol diglycidyl ether, resorcinol diglycidyl ether, 4,4'-methylenebis(N,N-diglycidylaniline), 3,4-epoxycyclohexylmethyl 3,4-epoxycyclohexanecarboxylate, 3,4-epoxy-1-cyclohexanecarboxylic acid, 3,4-epoxycyclohexan-1-yl) methyl ester, tert-butyl glycidyl ether, 2-Ethylhexyl glycidyl ether, epoxypropoxypropyl terminated polydimethylsiloxanes, neopentyl glycol diglycidyl ether, 1,4-cyclohexanedimethanol diglycidyl ether, 1,3-bis[2-(3,4-epoxycyclohexyl)ethyl]tetramethyldisiloxane, trimethylolpropane triglycidyl ether, diglycidyl 1,2-cyclohexanedicarboxylate, or the like, or a combination comprising at least one of the foregoing epoxy resins.

The adhesive layer can have a thickness of 2 to 50 micrometers, preferably 5 to 35 micrometers and more preferably 10 to 30 micrometers.

The second layer 106 contacts the either the first layer 102 at surface 103 or alternatively adhesive layer 104 at surface 105. The first layer 102 and the second layer 106 can comprise the same material or can comprise different materials. In an exemplary embodiment, the material used in the first layer 102 is different from the material used in the second layer 106. The material used in the second layer has a higher softening temperature than the softening temperature of the material used in the first layer as well as the softening temperature of the material used in the third layer. In an embodiment, the glass transition temperature of the material used in the second layer is greater than the glass transition temperature of the material used in the first layer.

The second layer 106 is also called the backing layer and provides strength and stability of the multilayer film 100 during the high temperatures experienced during the manufacturing process. The material used in second layer 106 has a softening point greater than or equal to 200° C., preferably greater than or equal to 225° C. and more preferably greater than or equal to 250° C.

In an embodiment, the second layer 106 comprises a polyimide, a polyetherimide, a polysulfone, a polyethersulfone, a polyketone, a polyether ether ketone, a polyether ketone ketone, a polybenzoxazole, a polyphthalamide, polyamides, or the like, or a combination thereof.

Examples of suitable materials used in the second layer 106 are polyimides. An exemplary commercially available polyimide is KAPTON® while a commercially available polyamide is NOMEX®.

In an embodiment, a second layer 106 may comprise a metal film or ceramic film so long as the metal or ceramic is flexible and can bend to permit the multilayer film 100 to wrap around a catheter having a circular cross-sectional area. Examples of metals are ductile metals such as steel, silver, aluminum, titanium, copper, or the like, or a combination thereof.

Examples of ceramics are metal oxides, a carbide, metal oxycarbides, metal nitrides, metal oxynitrides, metal borides, metal borocarbides, metal boronitrides, metal silicides, metal borosilicides, or the like, or a combination thereof.

Exemplary ceramics are silica, alumina, titania, zirconia, ceria, or the like, or a combination thereof.

In an embodiment, the second layer 106 has a plurality of expandable partitions 108 in it. The expandable partitions 108 extend from a free surface 107 that lies opposite to the surface 105 and extend through the length of the second layer 106 into the first layer 102 (when there is no third layer present) or into the third layer 104 and/or the first layer 102 when the third layer 104 is present. The term "free surface" implies that the surface 107 of the second layer 106 does not contact a surface of another layer and is in contact with ambient atmosphere when not being subjected to a manufacturing process.

The partitions 108 are slits that facilitate expansion of the outer circumference of the surface 107 of the layer 106 relative to the surface 101 when the multilayer tape 100 has to impart a texture to a curved surface. The partitions 108 may be filled with a thin layer of elastomer to prevent tearing.

Figure 4:
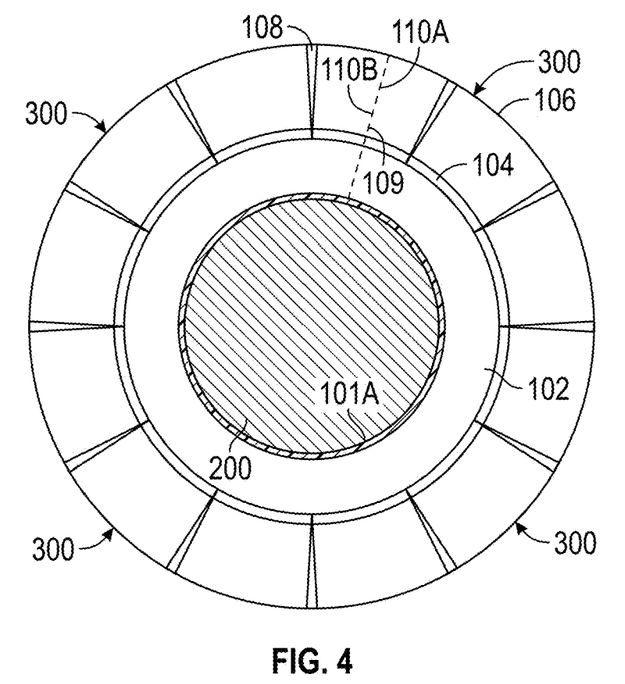
FIG. 4 depicts one exemplary embodiment of a cross-section of the multilayered tape when it is wound round an object having a curved surface.
Figure 5:
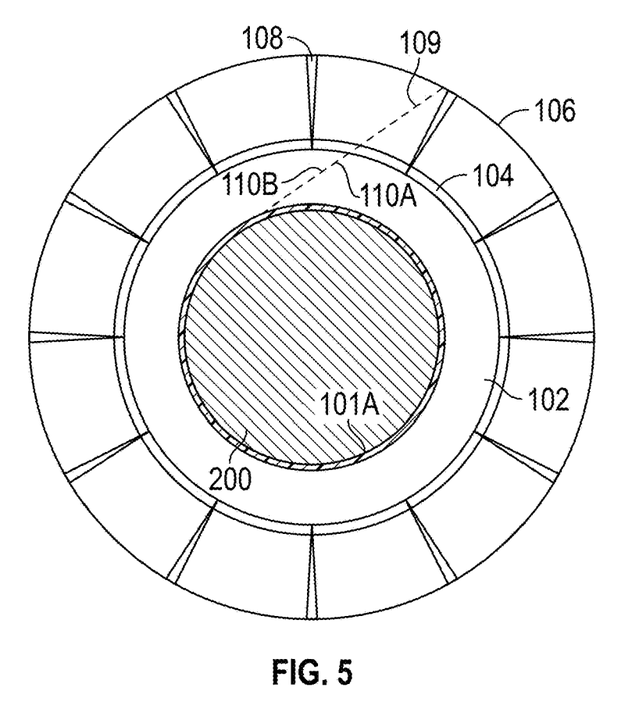
FIG. 5 depicts another exemplary embodiment of the cross-section of the multilayered tape when it is wound round an object having a curved surface.

The FIGS. 4 and 5 depict one embodiment of the use of the multilayer tape 100 to impart a texture to a curved surface such as, for example, the outer surface of a tube or a cylinder. When the multilayer tape 100 is disposed on the outer circumference of the cylinder or the tube 200, the layer 102 having surface texture 101A contacts the tube 200. The partitions 108 expand to accommodate the larger circumference that the outer surface 107 must occupy relative to the inner surface 101 in order to permit the inner surface 101 to contact the tube 200 evenly across its entire circumference. By applying a radial compressive force (such as, for example, via a die), uniformly across the outer surface of the multilayer tape 100 when it contacts the outer circumference of a cylinder or a tube as seen in the FIG. 4, texture can be transferred from surface texture 101A to the cylinder or the tube.

In the embodiment depicted in the FIG. 4, when the multilayer tape 100 is disposed on the outside of a cylinder or a conduit 200 to texture it, the ends 110A and 110B of the multilayer tape contact each other such that the surface texture 101A contacts the outer surface continuously and uniformly. It is desirable that the ends of the multilayer tape 110A and 110B do not overlap with each other when it is disposed on a device that is to be textured. The overlapping will lead to the formation of a mold line (also called a seam) (not shown) which will cause a surface defect.

In order to prevent the formation of a mold line because the width "R" of the tape (see FIG. 1) is not equal to the perimeter of the device that is to be textured, the ends 110A and 110B of the tape may be beveled as seen in the FIG. 5. When the beveled surfaces of the ends 110A and 110b are brought together during the manufacturing process, the surface of end 110A slips under the surface of end 110B thus preventing any overlap and damaging the surface of the device that is to be textured.

In an embodiment, in one method of manufacturing the multilayered tape 100, the first layer 102 is extruded and the desired pattern disposed on it using a template (not shown). The texture may be imparted to the tape first layer 102 in a continuous process. The second layer 106 may also be extruded in a separate extrusion step and then both the first layer 102 and the second layer 106 bonded together (laminated together) in a separate roll mill under pressure and/or heat.

In another embodiment, the first layer 102, the second layer 106 and the optional third layer 104 are coextruded and bonded together by laminating them in a roll mill under pressure. The first layer 104 of the laminate may then be textured by contacting it with a tape (a die) that has an image or a negative image of the desired texture.

In yet another embodiment, the first layer 102 is extruded and the desired pattern disposed on it using a template (not shown). The second and third layers 104 and 106 are then coextruded and laminated onto the first layer 102. In an embodiment, the third layer is cured using UV radiation. In another embodiment, the third layer is cured using thermal energy.

In one method of using the multilayer tape 100, a device (e.g., a conduit or cylinder whose outer surface is to be textured) is wrapped with the tape such that the longitudinal axis of the device is parallel to the longitudinal axis of the multilayered tape. The tape 100 contacts the device uniformly around its entire circumference in a single contact step and transfers its texture to the device while both the device and the tape are travelling in the longitudinal direction. By applying hydrostatic pressure uniformly to the tape 100, the texture is transferred from the tape to the device around its entire periphery. In short, the texture is imparted by the multilayered tape 100 to the entire circumferential surface of the device 200 (See FIGS. 4 and 5) during a single pass of both the multilayered tape 100 and the device 200 through a die.

The method of texturing is detailed in concurrently filed application having docket number SKT-0024, the entire contents of which are hereby incorporated by reference.

The devices to be textured generally comprise elastomers. Exemplary devices are catheters, tubes, cylinders, or the like. Examples of suitable elastomers are polydimethylsiloxane, polybutadiene, polyisoprene, styrene-butadiene-styrene (SBS), styrene-isoprene-styrene (SIS), styrene-ethylene/butylene-styrene (S-EB-S) block copolymers, thermoplastic polyurethanes, copolyester-ethers (block copolymers derived from terephthalic acid, polytetramethylene glycol, and 1,4-butanediol), natural rubber, synthetic polyisoprene, butyl rubber, halogenated butyl rubbers, polybutadiene, styrene-butadiene rubber, nitrile rubber, hydrogenated nitrile rubbers, chloroprene rubber, polychloroprene, ethylene propylene rubber, and ethylene propylene diene rubber, epichlorohydrin rubber, polyacrylic rubber, silicone rubber, fluorosilicone rubber, fluoroelastomers, perfluoroelastomers, polyether-block-polyamides, chlorosulfonated polyethylene, ethylene-vinyl acetate, or the like, or a combination comprising at least one of the foregoing block elastomers. An exemplary elastomer is a polysiloxane. It is desirable for the elastomer to have an elastic modulus of about $10^5$ pascals to about $10^8$ pascals.

The texture can also be used on the surfaces of body parts that are used in surgeries such as, for example, in a colostomy, and the like. The texture may also be used on the inner and outer surfaces of periodontal dressings; intravenous catheters and ports; foley catheters; surfaces in contact with tissues such as, for example, plates; adhesive tapes, patches, bandages, and the like; electronic leads; dental implants; orthodontia devices; iols (intraocular lenses); hydrogel films for tissue enhancement, skin grafting, isolation of bacteria or other microorganisms from tissues; heart-lung machine surfaces to reduce infection, clotting/thrombosis, enhance flow; tissue constructs for organ/tissue genesis; dialysis machine components, tubing and control panels; cochlear/otolaryngology implants and electronic devices; pace maker leads and body; fibrillator leads and body; heart valve flow surfaces and fixation surfaces; spinal implants; cranial/facial implants; biomedical instruments such as, for example, heart valves; scalpels; tongs; forceps; saws; reamers; grippers; spreaders; pliers; hammers; drills; laryngoscopes; bronchoscopes; oesophagoscopes; stethoscopes, mirrors, oral/ear speculum, xray plates/frames, xray device surfaces, magnetic resonance imaging (MRI) surfaces, echo cardiogram surfaces, cat-scan surfaces, scales, clipboards, and the like.

The multilayered tape 100 and the method of manufacturing the tape and using it is advantageous in that a texture can be imparted to devices having very small cross-sectional areas. The flexibility of the multilayered tape 100 permits imprinting surfaces having complicated shapes in a single pass. Entire surfaces of devices can be textured in a single contact with the tape. The device does not have to be subjected to multiple contacts with the tape 100 in order to texture it.

It is to be noted that as used herein, the terms "first," "second," and the like do not denote any order or importance, but rather are used to distinguish one element from another, and the terms "the", "a" and "an" do not denote a limitation of quantity, but rather denote the presence of at least one of the referenced item. Furthermore, all ranges disclosed herein are inclusive of the endpoints and independently combinable.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The transition phrase "comprising" is inclusive of the transition phrases "consisting essentially of" and "consisting of".

While the invention has been described in detail in connection with a number of embodiments, the invention is not limited to such disclosed embodiments. Rather, the invention can be modified to incorporate any number of variations, alterations, substitutions or equivalent arrangements not heretofore described, but which are commensurate with the scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A multilayered tape comprising:
a first layer; where the first layer comprises a first surface and second surface; the first surface of the first layer having a surface texture;
a second layer; the second layer having a first surface and a second surface; where the first surface of the second layer is closer to the second surface of the first layer than the second surface of the second layer; where the second surface of the second layer contains a plurality of slits that are parallel to a longitudinal direction of the multilayered tape and are operative to expand when the tape contacts a surface to which it imparts the surface texture.

2. The multilayered tape of claim 1, further comprising a third layer disposed between the first layer and the second layer where the third layer is operative to bond the first layer to the second layer.

3. The multilayered tape of claim 1, where the first layer has a lower softening temperature than the second layer.

4. The multilayered tape of claim 1, where the first layer has a softening temperature of greater than 130° C. and where the second layer has a softening temperature greater than 200° C.

5. The multilayered tape of claim 1, where the first layer comprises a polycarbonate and where the second layer comprises a polyimide.

6. The multilayered tape of claim 1, where the first layer comprises a polycarbonate and where the second layer comprises a metal or a ceramic.

7. The multilayered tape of claim 2, where the third layer comprises a silicone adhesive, an acrylate, an epoxy, or a combination thereof.

8. The multilayered tape of claim 1, where the third layer comprises a silicone adhesive.

9. The multilayered tape of claim 1, where the surface texture comprises a plurality of patterns; each pattern being defined by a plurality of spaced apart features; the plurality of features each having at least one neighboring feature having a substantially different geometry, wherein an average spacing between adjacent spaced apart features is about 1 nanometer to about 1 millimeter in at least a portion of the surface texture, wherein the plurality of spaced apart features are represented by a periodic function.

10. The multilayered tape of claim 1, where an end of the multilayered tape in the width direction is beveled.

11. The multilayered tape of claim 2, where the third layer is crosslinked.

12. A method comprising:
disposing a first layer on a second layer to form a multilayered tape; where the first layer comprises a first surface and second surface; the first surface of the first layer having a surface texture; and where the second layer comprises a first surface and a second surface; where the first surface of the second layer is closer to the second surface of the first layer than the second surface of the second layer; where the second surface of the second layer contains a plurality of slits that are parallel to a longitudinal direction of the multilayered tape and are operative to expand when the tape contacts a surface to which it imparts the surface texture; and
bonding the first layer to the second layer.

13. The method of claim 12, further comprising disposing a third layer between the first layer and the second layer.

14. A method comprising:
contacting a device with a multilayered tape, where the multilayered tape comprises:
a first layer; where the first layer comprises a first surface and second surface; the first surface of the first layer having a surface texture;
a second layer; the second layer having a first surface and a second surface; where the first surface of the second layer is closer to the second surface of the first layer than the second surface of the second layer; where the second surface of the second layer contains a plurality of slits that are parallel to a longitudinal direction of the multilayered tape and are operative to expand when the tape contacts a surface to which it imparts the surface texture;
transporting the device and a multilayered tape through a guide tube; the multilayered tape being disposed on an outer surface of a conduit, where the multilayered tape is placed between the conduit and the guide tube; where a longitudinal axis of the tape is substantially parallel to a longitudinal axis of the device; and
transferring a texture from the multilayered tape to the device as the device and the multilayer tape are transported through the guide tube.

15. The method of claim 14 where the device is a cylinder or a conduit having a circular cross-section.

16. The multilayered tape of claim 1, where the multilayered tape comprises two surface ends that are beveled such that one surface end can slip under the other surface end to prevent any overlap.

17. The method of claim 12, where the multilayered tape comprises two surface ends that are beveled such that one surface end can slip under the other surface end to prevent any overlap.

18. The method of claim 14, where the multilayered tape comprises two surface ends that are beveled such that one surface end can slip under the other surface end to prevent any overlap.

* * * * *